United States Patent
Richter et al.

(10) Patent No.: US 9,301,853 B2
(45) Date of Patent: Apr. 5, 2016

(54) HOLDER FOR IMPLANTATION AND EXTRACTION OF PROSTHESIS

(75) Inventors: Joern Richter, Kandern (DE); Roger Berger, Bueren (CH); Rudolf Bertagnoli, Vienna (AT)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/081,541

(22) Filed: Apr. 7, 2011

(65) Prior Publication Data
US 2011/0301612 A1 Dec. 8, 2011

Related U.S. Application Data

(63) Continuation-in-part of application No. 12/757,443, filed on Apr. 9, 2010, now Pat. No. 8,858,636.

(51) Int. Cl.
| | |
|---|---|
| A61B 17/70 | (2006.01) |
| A61F 2/46 | (2006.01) |
| A61F 2/44 | (2006.01) |
| A61F 2/30 | (2006.01) |

(52) U.S. Cl.
CPC ............ *A61F 2/4611* (2013.01); *A61F 2/4425* (2013.01); *A61F 2/3094* (2013.01); *A61F 2002/3093* (2013.01); *A61F 2002/30273* (2013.01); *A61F 2002/30275* (2013.01);
(Continued)

(58) Field of Classification Search
CPC ........... A61F 2/46; A61F 2/4611; A61F 2/44; A61F 2002/4622; A61F 2002/4625; A61F 2002/4627
USPC ...................... 606/99, 86 A; 623/17.11–17.16
See application file for complete search history.

(56) References Cited

U.S. PATENT DOCUMENTS 2,549,731 A * 4/1951 Wattley ......................... 439/482
4,877,020 A * 10/1989 Vich ............................ 606/86 R
(Continued)

FOREIGN PATENT DOCUMENTS

| EP | 1587461 | 4/2008 |
|---|---|---|
| WO | 00/49977 | 8/2000 |
| WO | 2006016384 | 2/2006 |
| WO | 2007038611 A2 | 4/2007 |
| WO | 2011/126490 | 10/2011 |

OTHER PUBLICATIONS

U.S. Official Action, dated Jan. 13, 2012, received in connection with related U.S. Appl. No. 12/757,443.
(Continued)

*Primary Examiner* — Jacqueline Johanas
(74) *Attorney, Agent, or Firm* — Meunier Carlin & Curfman LLC (57) ABSTRACT

Disclosed is an implant holder for an implant device comprising a locking mechanism that in a first position causes a clamp coupled to an implant device to lock such that the clamp cannot be decoupled from the implant device, and in a second position causes the clamp to unlock the implant device such that the clamp remains coupled to the implant device in the absence of a sufficient decoupling force but is decoupled from the implant device in the presence of a sufficient decoupling force. Also disclosed are methods of implanting an implant device using an implant holder by coupling the implant device to the implant holder, locking the implant device and the implant holder, emplacing the implant device utilizing the implant holder, unlocking the implant device and the implant holder such that the implant device is still coupled to the implant holder but can be decoupled with sufficient force.

22 Claims, 10 Drawing Sheets

(52) U.S. Cl.
CPC .............. *A61F2002/30326* (2013.01); *A61F 2002/30616* (2013.01); *A61F 2002/30649* (2013.01); *A61F 2002/30772* (2013.01); *A61F 2002/30787* (2013.01); *A61F 2002/30841* (2013.01); *A61F 2002/30843* (2013.01); *A61F 2002/30848* (2013.01); *A61F 2002/443* (2013.01); *A61F 2002/4622* (2013.01); *A61F 2002/4624* (2013.01); *A61F 2002/4628* (2013.01); *A61F 2002/4629* (2013.01); *A61F 2310/00017* (2013.01); *A61F 2310/00023* (2013.01); *A61F 2310/00029* (2013.01); *A61F 2310/00179* (2013.01); *A61F 2310/00796* (2013.01)

(56) References Cited

U.S. PATENT DOCUMENTS

| | | | |
|---|---|---|---|
| 4,997,432 A * | 3/1991 | Keller | 623/17.11 |
| 5,071,437 A | 12/1991 | Steffee | |
| 5,306,309 A | 4/1994 | Wagner et al. | |
| 5,443,514 A * | 8/1995 | Steffee | 128/898 |
| 5,522,899 A | 6/1996 | Michelson | |
| 5,676,701 A | 10/1997 | Yuan et al. | |
| 5,683,464 A | 11/1997 | Wagner et al. | |
| 5,888,227 A | 3/1999 | Cottle | |
| 6,066,174 A * | 5/2000 | Farris | 606/206 |
| 6,159,215 A * | 12/2000 | Urbahns et al. | 606/86 R |
| 6,267,763 B1 | 7/2001 | Castro | |
| 6,319,257 B1 * | 11/2001 | Carignan et al. | 606/99 |
| 6,416,551 B1 | 7/2002 | Keller | |
| 6,440,142 B1 | 8/2002 | Ralph et al. | |
| 6,440,168 B1 | 8/2002 | Cauthen | |
| 6,517,580 B1 | 2/2003 | Ramadan et al. | |
| 6,740,118 B2 | 5/2004 | Eisermann et al. | |
| 6,827,740 B1 | 12/2004 | Michelson | |
| 6,936,071 B1 | 8/2005 | Marnay et al. | |
| 6,966,929 B2 | 11/2005 | Mitchell | |
| 6,994,727 B2 | 2/2006 | Khandkar et al. | |
| 7,051,417 B2 | 5/2006 | Michelson | |
| 7,105,024 B2 | 9/2006 | Richelsoph | |
| 7,115,143 B1 | 10/2006 | Michelson | |
| 7,166,129 B2 | 1/2007 | Michelson | |
| 7,198,644 B2 | 4/2007 | Schultz et al. | |
| 7,204,852 B2 | 4/2007 | Marnay et al. | |
| 7,217,292 B2 | 5/2007 | Ralph et al. | |
| 7,235,103 B2 | 6/2007 | Rivin | |
| 7,244,275 B2 | 7/2007 | Michelson | |
| 7,273,496 B2 | 9/2007 | Mitchell | |
| 7,300,465 B2 | 11/2007 | Paul et al. | |
| 7,331,995 B2 | 2/2008 | Eisermann et al. | |
| 7,364,589 B2 | 4/2008 | Eisermann | |
| 7,442,211 B2 | 10/2008 | de Villiers et al. | |
| 7,517,363 B2 | 4/2009 | Rogers et al. | |
| 7,563,286 B2 | 7/2009 | Gerber et al. | |
| 7,594,919 B2 * | 9/2009 | Peterman | 606/99 |
| 7,618,423 B1 * | 11/2009 | Valentine et al. | 606/99 |
| 7,686,809 B2 * | 3/2010 | Triplett et al. | 606/86 A |
| 7,846,210 B2 * | 12/2010 | Perez-Cruet et al. | 623/17.16 |
| 7,850,736 B2 | 12/2010 | Heinz | |
| 7,891,434 B2 | 2/2011 | Gaudette et al. | |
| 8,142,435 B2 * | 3/2012 | Refai et al. | 606/86 A |
| 8,197,484 B2 * | 6/2012 | Sato et al. | 606/86 B |
| 8,235,997 B2 * | 8/2012 | Hoffman et al. | 606/86 A |
| 8,486,081 B2 * | 7/2013 | Parsons et al. | 606/99 |
| 8,906,033 B2 | 12/2014 | DiMauro et al. | |
| 2001/0019816 A1 | 9/2001 | Kumar | |
| 2004/0147937 A1 * | 7/2004 | Dunbar et al. | 606/99 |
| 2004/0172133 A1 | 9/2004 | Gerber et al. | |
| 2004/0254643 A1 | 12/2004 | Jackson | |
| 2005/0021042 A1 * | 1/2005 | Marnay et al. | 606/99 |
| 2005/0027362 A1 | 2/2005 | Williams et al. | |
| 2005/0033305 A1 * | 2/2005 | Schultz | 606/99 |
| 2005/0038445 A1 * | 2/2005 | Errico et al. | 606/99 |
| 2005/0131544 A1 | 6/2005 | Kuras et al. | |
| 2005/0143749 A1 * | 6/2005 | Zalenski et al. | 606/99 |
| 2005/0197706 A1 | 9/2005 | Hovorka et al. | |
| 2005/0240267 A1 | 10/2005 | Randall et al. | |
| 2005/0251260 A1 | 11/2005 | Gerber et al. | |
| 2005/0273171 A1 | 12/2005 | Gordon et al. | |
| 2005/0288788 A1 | 12/2005 | Dougherty-Shah | |
| 2006/0025777 A1 * | 2/2006 | Weber | 606/99 |
| 2006/0030860 A1 * | 2/2006 | Peterman | 606/99 |
| 2006/0074418 A1 * | 4/2006 | Jackson | 606/61 |
| 2006/0129241 A1 | 6/2006 | Boyer et al. | |
| 2006/0235535 A1 | 10/2006 | Ferree et al. | |
| 2006/0293690 A1 * | 12/2006 | Abdelgany | 606/103 |
| 2007/0010887 A1 | 1/2007 | Williams et al. | |
| 2007/0013311 A1 | 1/2007 | Moon et al. | |
| 2007/0072475 A1 | 3/2007 | Justin et al. | |
| 2007/0073311 A1 * | 3/2007 | Williams et al. | 606/108 |
| 2007/0093900 A1 | 4/2007 | Williams et al. | |
| 2007/0100347 A1 | 5/2007 | Stad et al. | |
| 2007/0100455 A1 | 5/2007 | Parsons | |
| 2007/0112429 A1 | 5/2007 | Muhanna et al. | |
| 2007/0123907 A1 * | 5/2007 | Weber | 606/99 |
| 2007/0156239 A1 | 7/2007 | Zipnick et al. | |
| 2007/0255407 A1 | 11/2007 | Castleman et al. | |
| 2007/0255414 A1 | 11/2007 | Melkent et al. | |
| 2007/0255416 A1 | 11/2007 | Melkent et al. | |
| 2007/0270956 A1 | 11/2007 | Heinz | |
| 2007/0282441 A1 | 12/2007 | Stream et al. | |
| 2007/0299521 A1 | 12/2007 | Glenn et al. | |
| 2008/0015698 A1 | 1/2008 | Marino et al. | |
| 2008/0103598 A1 | 5/2008 | Trudeau et al. | |
| 2008/0200984 A1 * | 8/2008 | Jodaitis et al. | 623/17.16 |
| 2008/0255574 A1 * | 10/2008 | Dye | 606/99 |
| 2008/0275447 A1 * | 11/2008 | Sato et al. | 606/65 |
| 2008/0275455 A1 * | 11/2008 | Berry et al. | 606/99 |
| 2008/0287957 A1 * | 11/2008 | Hester et al. | 606/99 |
| 2008/0294173 A1 | 11/2008 | Reeder et al. | |
| 2008/0306488 A1 * | 12/2008 | Altarac et al. | 606/99 |
| 2008/0306557 A1 * | 12/2008 | Altarac et al. | 606/86 A |
| 2009/0012529 A1 | 1/2009 | Blain et al. | |
| 2009/0018661 A1 | 1/2009 | Kim et al. | |
| 2009/0030421 A1 * | 1/2009 | Hawkins et al. | 606/99 |
| 2009/0030422 A1 * | 1/2009 | Parsons et al. | 606/99 |
| 2009/0112217 A1 | 4/2009 | Hester | |
| 2009/0216330 A1 * | 8/2009 | Geisert et al. | 623/17.16 |
| 2009/0228054 A1 * | 9/2009 | Hoffman et al. | 606/86 A |
| 2009/0254182 A1 * | 10/2009 | Kovarik et al. | 623/17.11 |
| 2010/0023019 A1 * | 1/2010 | Fuhrer et al. | 606/99 |
| 2010/0023128 A1 * | 1/2010 | Malberg | 623/17.16 |
| 2010/0042216 A1 | 2/2010 | Kilpela et al. | |
| 2010/0057205 A1 | 3/2010 | Justin et al. | |
| 2010/0121388 A1 * | 5/2010 | Flickinger et al. | 606/86 A |
| 2010/0168803 A1 * | 7/2010 | Hestad et al. | 606/86 A |
| 2010/0191241 A1 * | 7/2010 | McCormack et al. | 606/83 |
| 2010/0249795 A1 * | 9/2010 | DiMauro et al. | 606/99 |
| 2010/0268343 A1 | 10/2010 | Dewey et al. | |
| 2010/0280618 A1 * | 11/2010 | Jodaitis et al. | 623/17.16 |
| 2010/0286778 A1 | 11/2010 | Eisermann et al. | |
| 2010/0286784 A1 * | 11/2010 | Curran et al. | 623/17.16 |
| 2010/0331901 A1 * | 12/2010 | Iott et al. | 606/86 A |
| 2010/0331985 A1 | 12/2010 | Gordon et al. | |
| 2011/0015678 A1 * | 1/2011 | Jackson | 606/264 |
| 2011/0251690 A1 | 10/2011 | Berger et al. | |
| 2012/0150241 A1 * | 6/2012 | Ragab et al. | 606/86 A |

OTHER PUBLICATIONS

Official U.S. Office Action, dated Jun. 6, 2013, in connection with related U.S. Appl. No. 12/757,443.
Official U.S. Office Action, dated Jun. 18, 2012, in connection with related U.S. Appl. No. 12/757,443.
International Search Report and Written Opinion, dated Jan. 12, 2011, in connection with related International Application No. PCT/US2010/030523.
Related U.S. Appl. No. 12/757,443, filed Apr. 9, 2010.
International Search Report and Written Opinion, dated Jan. 12, 2011, in International Application No. PCT/US2010/030523.

* cited by examiner

HOLDER FOR IMPLANTATION AND EXTRACTION OF PROSTHESIS

CROSS-REFERENCE TO RELATED APPLICATIONS

This application is a continuation-in-part of U.S. patent application Ser. No. 12/757,443. entitled "Intervertebral Implant" (filed Apr. 9, 2010), the contents of which are incorporated herein by reference in their entirety.

BACKGROUND

Historically, complete removal of a disc from between adjacent vertebrae resulted in the need to immovably fuse the adjacent vertebrae together, and this "spinal fusion" procedures is still used today as a widely-accepted surgical treatment for disc removal stemming from, for example, a degenerative disc disease or disc injury. However, in many instances, disc arthoplasty—the insertion of an artificial intervertebral disc into the intervertebral space between adjacent vertebrae—may be preferable to spinal fusion as the former may help preserve some limited universal movement of the adjacent vertebrae with respect to each other whereas the latter does not. As such, the objective of total disc replacement is not only to diminish pain caused by a degenerated disc, but also to restore anatomy (disc height) and maintain mobility in the functional spinal unit so that the spine remains in an adapted "sagittal balance" (the alignment equilibrium of the trunk, legs, and pelvis necessary to maintain the damping effect of the spine).

Several forms of intervertebral implants include an upper part mounted to an adjacent vertebra, a lower part mounted to another adjacent vertebra, and a rotation-assist insert located between these two parts. In addition these intervertebral implants are often very small—perhaps ten millimeters wide and a few millimeters high—and are thus difficult for surgeons to hold, orient, and emplace when using just their fingers. Nevertheless, implantation of these intervertebral devices (or "implant devices") requires precise and careful emplacement in order to ensure correction functioning.

SUMMARY

To assist with the correct emplacement of an implant device, an insertion tool comprising an implant holder may be utilized. Generally the implant holder must be able to firmly affix to the implant device in order to allow the surgeon to use the necessary pressure and force required to properly emplace the implant device, but then disengage from the implant device once the implant device is correctly positioned and enable the implant holder to be completely withdrawn.

Disclosed herein are various embodiments directed to an implant holder for an implant device comprising a clamp for coupling to and decoupling from the implant device, and a locking mechanism that, in a first position, causes the clamp to lock the implant device such that the clamp cannot be decoupled from the implant device, and in a second position, causes the clamp to unlock the implant device such that the clamp remains coupled to the implant device in the absence of a sufficient decoupling force (such as a surgeon force, defined later herein) but is decoupled from the implant device in the presence of a sufficient decoupling force.

Also disclosed herein are several methods of implanting an implant device using an implant holder comprising coupling the implant device to the implant holder, locking the implant device and the implant holder, emplacing the implant device utilizing the implant holder, unlocking the implant device and the implant holder such that the implant device is still coupled to the implant holder, and uncoupling the implant device from the implant holder and withdrawing the implant holder.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In addition, various components are described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. For instance, when an implant is emplaced into an intervertebral space, the transverse direction T extends generally along the superior-inferior (or caudal-cranial) direction, while the plane defined by the longitudinal direction L and the lateral direction A lie generally in the anatomical plane defined by the anterior-posterior direction and the medial-lateral direction. Accordingly, the directional terms "vertical" and "horizontal" are used to describe the components merely for the purposes of clarity and illustration and are not meant to be limiting.

Figure 1A:
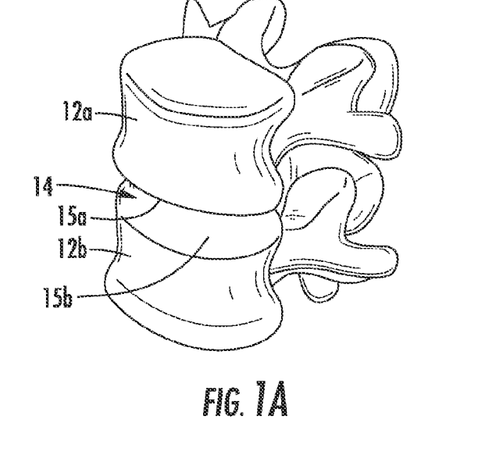
FIG. 1A is a perspective view of a pair of vertebral bodies separated by an intervertebral space.
Figure 1B:
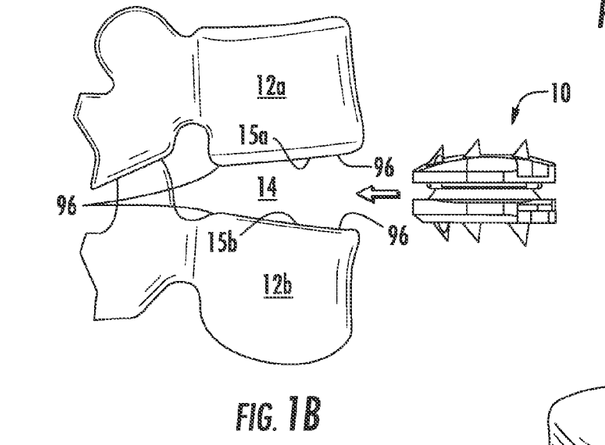
FIG. 1B is a side elevation view illustrating the insertion of an intervertebral implant into the intervertebral space between the two vertebral bodies of FIG. 1A.
Figure 1C:
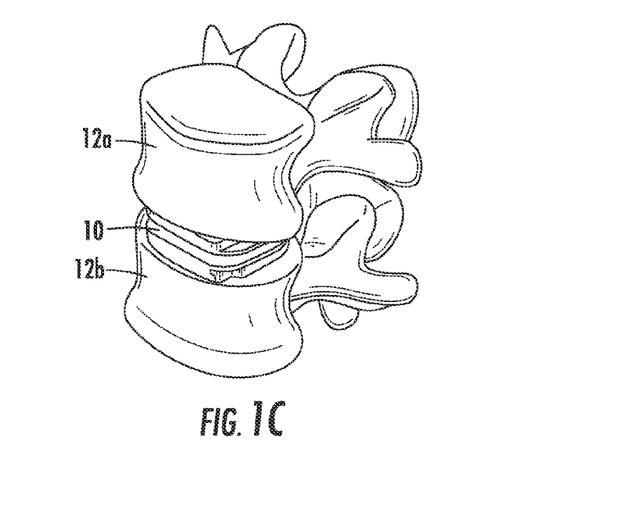
FIG. 1C is a perspective view of the vertebral bodies of FIGS. 1A and 1B with an intervertebral implant inserted into the intervertebral space.

FIG. 1A is a perspective view of a pair of vertebral bodies 12a and 12b separated by an intervertebral space 14. FIG. 1B is a side elevation view illustrating the insertion of an intervertebral implant 10 into the intervertebral space 14 between the two vertebral bodies 12a and 12b of FIG. 1A. FIG. 1C is a perspective view of the vertebral bodies 12a and 12b of FIGS. 1A and 1B with the intervertebral implant 10 inserted into the intervertebral space 14.

Referring to FIGS. 1A, 1B, and 1C (collectively referred to herein as "FIG. 1"), a superior vertebral body 12a defines a superior vertebral surface 15a of an intervertebral space 14, and an adjacent inferior vertebral body 12b defines an inferior vertebral surface 15b of the intervertebral space 14. The intervertebral space 14 may be created by a discectomy where the disc material (not shown) normally found between the two vertebral bodies 12a and 12b has been removed to prepare the intervertebral space 14 to receive an orthopedic implant such as, for example, the intervertebral implant 10.

During operation the implant 10 is aligned with the intervertebral space 14. The vertebral bodies 12a and 12b are retracted such that the anterior ends 96 of the vertebral bodies are separated generally along the caudal-cranial dimension a distance greater than the posterior ends 98 of the vertebral bodies 12a and 12b are separated. The implant 10 may then be inserted into the intervertebral space 14 to achieve restoration of "height" (that is, anatomically correct separation of the superior vertebral surface 15a from inferior vertebral surface 15b) while maintaining mobility.

Figure 2A:
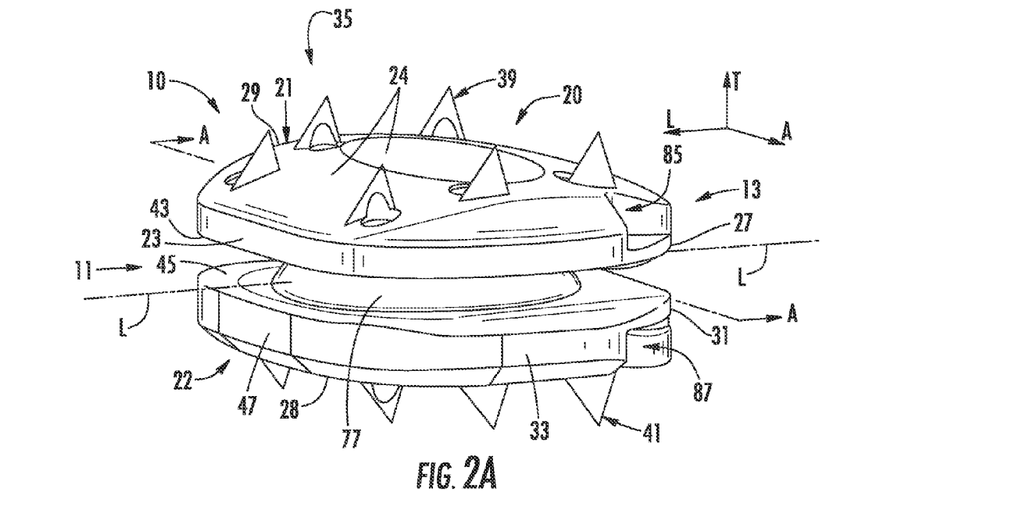
FIG. 2A is a perspective view of the intervertebral implant illustrated in FIG. 1B which includes first and second endplates and an articulation disposed between the endplates.
Figure 2B:
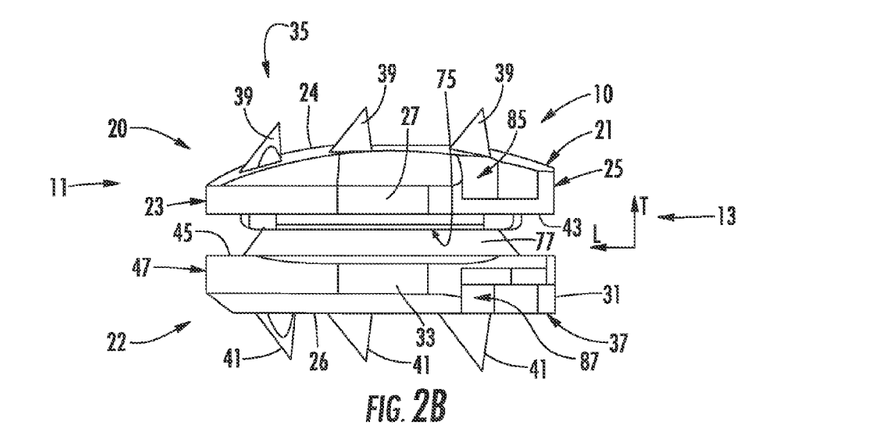
FIG. 2B is a side elevation view of the intervertebral implant illustrated in FIG. 2A.

FIG. 2A is a perspective view of the intervertebral implant 10 illustrated in FIG. 1B which includes first and second endplates (20 and 22 respectively) together forming an articulation disposed between the endplates. FIG. 2B is a side elevation view of the intervertebral implant illustrated in FIG. 2A.

Referring now to FIGS. 2A and 2B (collectively referred to herein as "FIG. 2"), and with reference to FIG. 1, the implant 10 may include a first or upper component, such as a first or upper endplate 20 adapted to engage the superior vertebral body 12a, and a second or lower component, such as a second or lower endplate 22 adapted to engage the inferior vertebral body 12b. The endplates 20 and 22 each carry complementary first and second joint members 75 and 77, respectively, that provide rounded mating surfaces (concave for joint member 75 and convex for joint member 77) in operative contact with each other so as to provide an articulating joint that allows the endplates 20 and 22 360-degree universal movement relative to each other. The upper and lower endplates 20 and 22 can thus pivot relative to each other about a lateral axis, for instance to accommodate flexions and extensions of the vertebrae 12a and 12b. Similarly, the upper and lower endplates 20 and 22 can pivot relative to each other about a longitudinal axis, for instance to accommodate lateral bending of the vertebrae 12a and 12b. The pivot axis can also lie in any orientation within the horizontal plane defined by the longitudinal and lateral directions.

In addition to the concave mating surfaces 75, the upper endplate 20 also comprises an upper endplate body 21 that defines a longitudinally front end 23, which provides a leading end with respect to insertion of the implant 10 into the intervertebral disc space 14. The upper endplate body 21 further defines an opposing longitudinal rear end 25, which provides a trailing end with respect to insertion of the implant 10 into the intervertebral disc space 14. The upper endplate body 21 further defines opposing first and second lateral sides 27 and 29, respectively, connected between the front and rear ends 23 and 25 respectively. The upper endplate body 21 further presents an upper (or outer) transverse bone facing surface 24, and an opposing lower (or inner) transverse surface 43. The upper endplate 20 includes a plurality of bone fixation spikes 39 projecting transversely outward, or up, from the bone facing surface 24 of the upper endplate body 21.

Similarly, in addition to the convex mating surfaces 77, the lower endplate 22 also comprises a lower endplate body 37 that defines a longitudinally front end 47, which provides a leading end with respect to insertion of the implant 10 into the intervertebral disc space 14. The lower endplate body 37 further defines an opposing longitudinal rear end 31, which provides a trailing end with respect to insertion of the implant 10 into the intervertebral disc space 14. The lower endplate body 37 further defines opposing first and second lateral sides 33 and 35, respectively, connected between the front and rear ends 47 and 31 respectively. The lower endplate body 37 further presents a lower (or outer) transverse bone facing surface 26, and an opposing upper (or inner) transverse surface 45. The lower endplate 22 includes a plurality of bone fixation spikes 41 projecting transversely outward, or down, from the bone facing surface 26 of the lower endplate body 37.

The front ends 23 and 47 of the endplates 20 and 22 define the front end 11 of the implant 10 corresponding to the posterior of the intervertebral space 14 for emplacement, while the rear ends 25 and 31 of the endplates 20 and 22 define the back end 13 of the implant 10 corresponding to the opposing anterior of the intervertebral space 14 for emplacement. Otherwise stated, the front end 11 is emplaced into the posterior region (proximate to posterior ends 98) of the intervertebral space 14 and the back end 13 is emplaced into the anterior region (proximate to anterior ends 96) of the intervertebral space 14.

To facilitate emplacement using an implant holder (various embodiments of which are described in detail later herein), the upper endplate 20 includes laterally opposing notches 85 that are external engagement features extending into the rear end 25 of the endplate body 21 that are sized and shaped to receive the upper portion of the distal end of an insertion tool (or implant holder) configured to insert the implant into an intervertebral space. The lower endplate 22 includes laterally opposing notches 87 extending into the rear end 31 of the endplate body 37 that are sized and shaped to receive the lower portion of an insertion tool configured to insert the implant 10 into an intervertebral space.

As the implant 10 is inserted into the intervertebral space 14, the spikes 39 and 41 initially slide freely into the intervertebral space 14, and prior to full insertion begin to bite into the respective vertebral surfaces 15a and 15b. Once the implant 10 has been fully inserted into the intervertebral space 14, the retraction of the vertebral bodies 12a and 12b is released, thereby causing the surfaces 15a and 15b to return to their normal direction of extension, whereby the spikes 39 and 41 project into the vertebral surfaces 15a and 15b.

Since it may be challenging to manually handle the implant 10 because of its small size (e.g., less than ten millimeters wide, ten millimeters long, and only a few millimeters thick), a separate instrument—referred to as an implant holder or insertion tool—may be used to emplace the vertebral implant 10. In general, the implant 10 is fixed to the implant holder, and then the surgeon directly manipulates the implant holder to emplace the implant 10 (without ever directly touching the implant in some embodiments). When the implant 10 is seemingly in place, the surgeon then uses X-rays to check position of the implant 10 (typically in profile) to see whether the implant 10 is properly placed or whether it must still be further maneuvered into a better position, and the surgeon adjusts the implants position as necessary by continuing to manipulate the implant holder. Once the desired emplacement of the implant 10 is seemingly achieved, the implant holder is then detached from the implant 10 and withdrawn, leaving behind the emplaced implant 10.

Various implant holders are disclosed herein comprise three functional components: a clamp, a sleeve, and a shaft. While these components are disclosed as distinct, separate, and interchangeable pieces that can be operatively coupled together for utilization, it will be readily understood and appreciated that these three functional components can also be formed as a single tool wherein the components are inseparable, or as a two-part tool wherein any two of the three operational components are formed as a single item. Similarly, an optional fourth component—an emplacement stop system—is also herein disclosed as a separate fourth piece for use with the implant holder but which can also be formed as part of the implant holder (namely the sleeve). Accordingly, nothing herein is intended to limit the embodiments described herein to separable components but, instead, a single formed piece may comprise one or more than one of the operational components described herein.

Figure 3A:
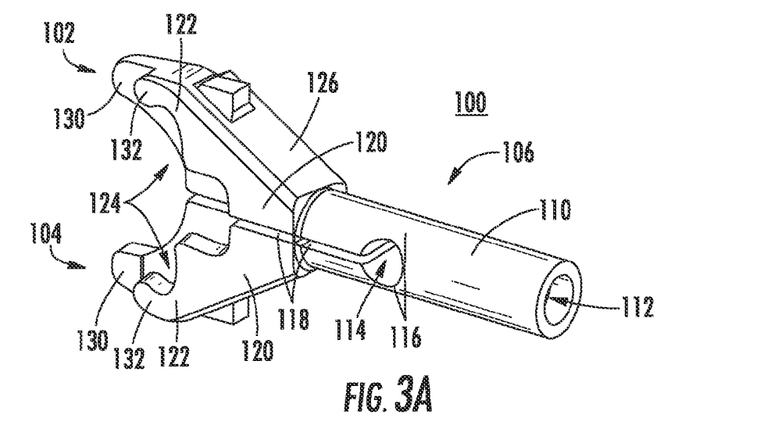
FIG. 3A is a perspective view of an exemplary implementation of an implant holder clamp utilized by several implant holder embodiments disclosed herein.
Figure 3B:
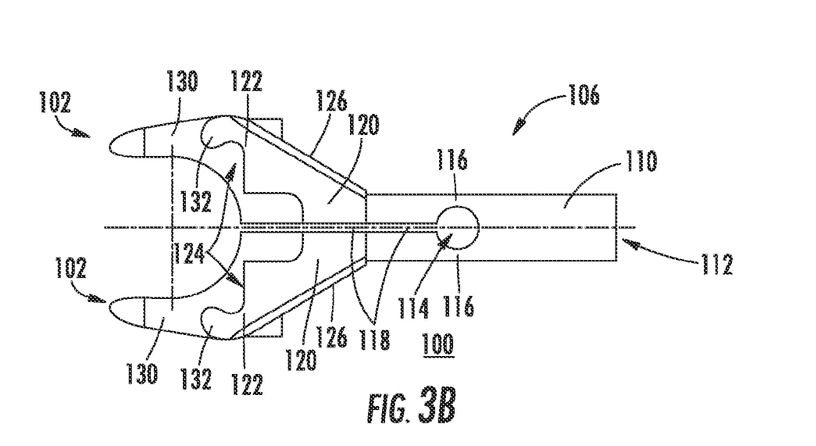
FIG. 3B is a top elevation view of the exemplary implementation of the clamp of FIG. 3A.
Figure 3C:
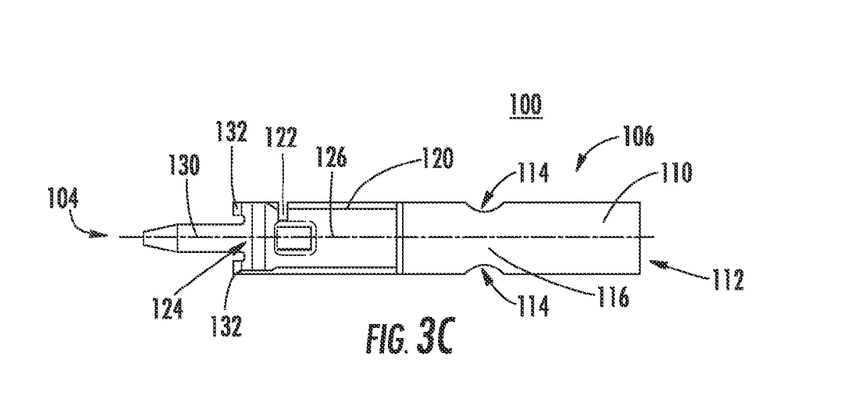
FIG. 3C is a side elevation view of the exemplary implementation of the clamp of FIGS. 3A and 3B.

FIG. 3A is a perspective view of an exemplary implementation of an implant holder clamp 100 (or clamp) utilized by several implant holder embodiments disclosed herein. FIG. 3B is a top elevation view of the exemplary implementation of the clamp 100 of FIG. 3A. FIG. 3C is a side elevation view of the exemplary implementation of the clamp 100 of FIGS. 3A and 3B.

Referring to FIGS. 3A, 3B, and 3C (collectively referred to herein as "FIG. 3"), the implant holder clamp 100 essentially comprises a U-shaped fork with two arms 102 and 104 fixedly coupled to a stem 106. As illustrated, the stem 106 may comprise a substantially solid rod 110 with a shallow threaded hole 112 at the proximal end for attaching to the threaded end of a shaft. The stem is also fixedly coupled to each arm 102 and 104 proximate to a flexion hole 114. The arms 102 and 104 are separated from each other by the flexion hole 114 and by a lateral gap 118 running from the flexion hole 114 to the distal end of the clamp 100. Moreover, each arm 102 and 104 comprises a flexion portion 116—in part formed by the flexion hole 114—which provides the arms 102 and 104 with limited flexibility such that they can be moved toward or away from each other relative to their resting position (as illustrated) with the application of force (which also has the effect of decreasing or increasing the width of the lateral gap 118 running between the arms 102 and 104).

The amount of force necessary to slightly separate the two arms 102 and 104 is dependent upon the thickness of the flexion portion 116 and the material from which the flexion portions (and, ostensibly, the entire stem) is made. For various embodiments disclosed herein, the amount of force required is low enough to enable a surgeon of ordinary strength and dexterity to affix an implant 10 onto the arms 102 and 104 of the implant holder clamp 100 as well as enable the implant 10 to detach and remain in position when emplaced in the intervertebral space 14 as the implant holder clamp 100 is withdrawn using a retraction force applied by the surgeon, but yet high enough to prevent the implant 10 from becoming inadvertently detached from the implant holder clamp 100 such as while the implant 10 is being emplaced in a forward longitudinal direction using the implant holder clamp 100. This force is hereafter referred to as a "surgeon force" and an implant 10 that is attached and detached to an implant holder clamp 100 using surgeon force is said to be "loosely coupled." In contrast, and as described later herein, when the implant cannot be decoupled from the implant holder using surgeon force, the implant is said to be "fixedly coupled."

Referring again to FIG. 3, each arm 102 and 104 further comprises a central body 120 featuring two of four clamping elements 132 (one superior and one inferior), half of a U-shaped central spacer 130, and one of a pair of locking surfaces 126, and a projection extending from and contained on each of the pair of locking surfaces. In normal operation, the four central-projecting clamping elements 132 are able to engage the notches 85 and 87 of the implant device 10 with the application of surgeon force as previously described. However, the locking surfaces 126 of each arm 102 and 104 enable the application of a locking force (for example, by operation of the shaft and sleeve discussed later herein) to fixedly couple the implant 10 to the clamp 100 by preventing the arms 102 and 104 from flexibly opening. Separately, the U-shaped central spacer 130 formed by both arms 102 and 104 semi-circumferentially abut against the convex joint member 77 of the articulating joint of the implant 10 as well as the upper and lower endplates 20 and 22 in order to maintain in parallel the lower (or inner) transverse surface 43 of the upper endplate 20 and the upper (or inner) transverse surface 45 of the lower endplate 22 to give temporary solidity to the implant 10 during its emplacement.

In addition, each arm also comprises an optical control channel 122 on the upper surface of the arms 102 and 104 to enable the surgeon to visually gauge the location of the back end 13 of the implant 10 when the surgeon uses X-rays to check position of the implant 10 in profile (or laterally). For example, when the clamp 100 and the implant 10 are both made of radio-opaque materials (or any other situation where it is difficult to tell apart the implant 10 from the clamp 100 using X-rays), this optical control channel 122 provides an X-ray-visible feature that enables the surgeon to differentiate between the two components and better determine how far the back end 13 of the implant 10 is embedded (or "implanted" or "emplaced") in the intervertebral space 14. To this end, the optical control channel 122 may simply comprise a straight line-of-sight channel (with the arms in the resting position) or, alternatively, it may be coated or filled with X-ray reflective or deflective material to make it even more easily identified using an X-ray. Likewise, the channel may also be shaped differently—such as, for example, narrower medially but wider laterally to provide a less-specific by easier-to-identify reference point—and/or the clamp 100 may comprise more than one channel—such as, for example, a second optical control channel running on the lower endplate running parallel to the first optical control channel 122.

Figure 4A:
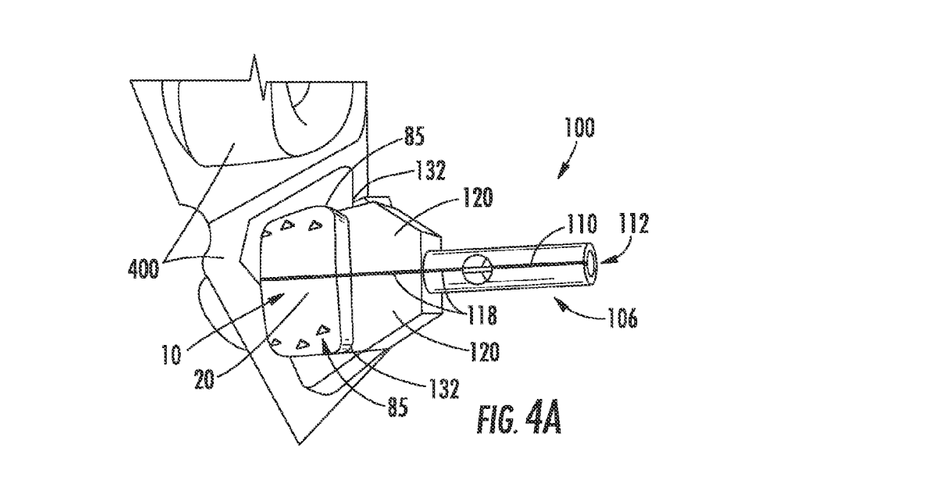
FIG. 4A is a perspective view of the implant holder clamp of FIGS. 3A, 3B, and 3C being coupled to an intervertebral implant of FIGS. 2A and 2B (the latter still housed in sterile packaging)
Figure 4B:
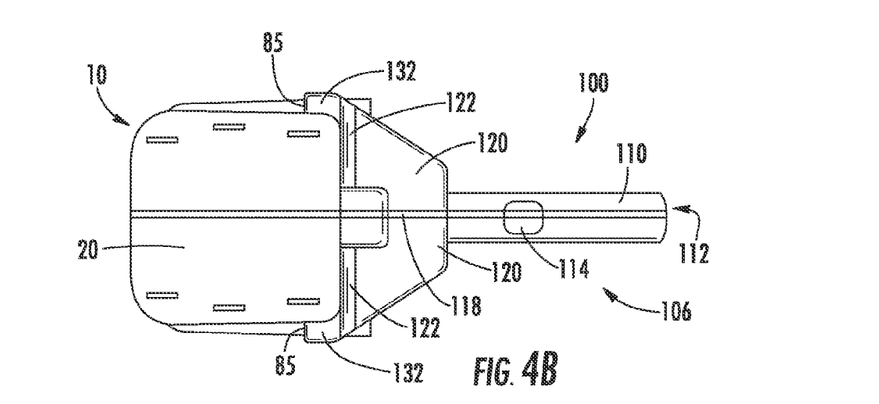
FIG. 4B is a top view of the implant holder coupled to the intervertebral implant (and together removed from the sterile packaging of FIG. 4A)
Figure 4C:
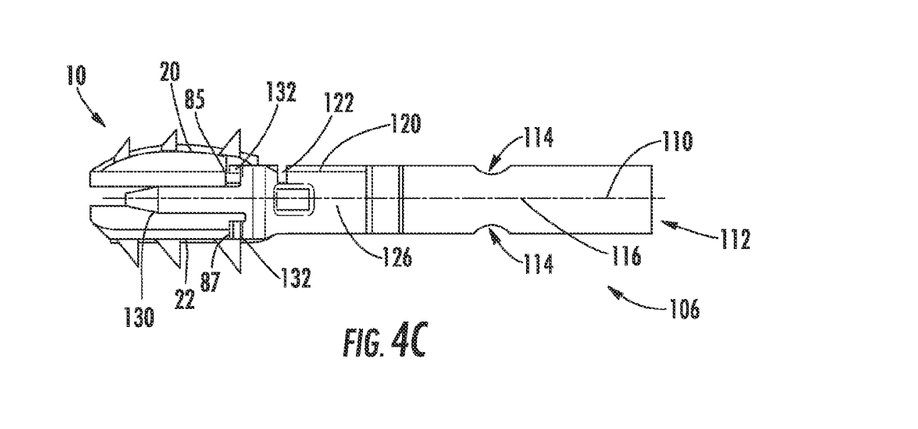
FIG. 4C is a side elevation view of the implant holder coupled to the intervertebral implant illustrated in FIG. 4B.

FIG. 4A is a perspective view of the implant holder clamp 100 of FIGS. 3A, 3B, and 3C being coupled to an intervertebral implant 10 of FIGS. 2A and 2B (the latter still housed in sterile packaging 400. FIG. 4B is a top view of the implant holder 100 coupled to the intervertebral implant 10 (and together removed from the sterile packaging 400 of FIG. 4A). FIG. 4C is a side elevation view of the implant holder 10 coupled to the intervertebral implant 10 illustrated in FIG. 4B. Referring to FIGS. 4A, 4B, and 4C (collectively referred to herein as "FIG. 4"), the implant 10 is removed from its sterile packing longitudinally moving the implant holder 100 with surgeon force to loosely couple with the implant and then retracting the implant holder 100 and the implant 10 from the packaging—which, as illustrated, may be accomplished without the person performing the coupling directly touching the implant 10. With particular reference to FIG. 4B, it should be noted that the left edge of the optical control channel 122 of the implant holder 100 is substantially aligned with the back end 13 of the implant 10 such that the back end 13 of the implant can be accurately determined by locating the optical control channel 122 during the surgeon's aforementioned X-ray checks.

Figure 5:
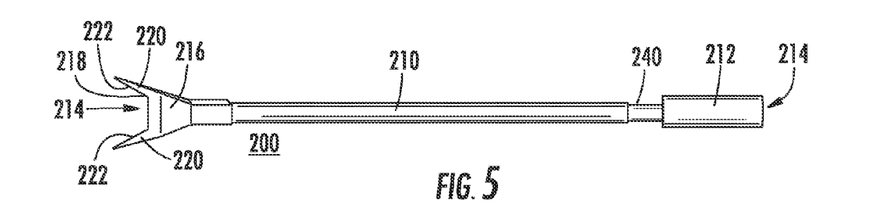
FIG. 5 a top view of an exemplary implementation of an implant holder sleeve (or guide member) utilized by several implant holder embodiments disclosed herein.

FIG. 5 a top view of an exemplary implementation of an implant holder sleeve (or guide member) 200 utilized by several implant holder embodiments disclosed herein. Referring to FIG. 5, the sleeve 200 comprises a hollow body 210 featuring, at its proximal end, an attachment surface 240, a service collar 212, and the proximal opening of the hollow channel 214 running the length of the sleeve 200. The attachment surface 240 may be used for mounting supplemental devices to the sleeve 200 (such as the stop system discussed later herein, for example). At the distal end, the hollow body 210 features a clamp coupler 216 which in turn comprises two locking tines 220 and the distal opening of the hollow channel 214 in a terminus surface 218. The two locking tines 220 each comprise a locking surface 222 that are together geometrically angled to substantially match the geometric angle of the two locking surfaces 126 of the implant holder clamp 100. Each of the locking surfaces 222 can include a recess for receiving the corresponding projection extending from locking surfaces 126.

Figure 6:
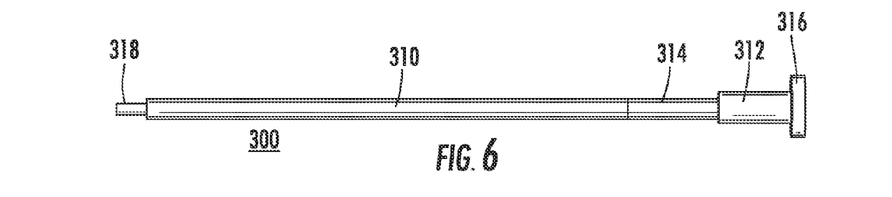
FIG. 6 a top view of an exemplary implementation of an implant holder shaft (or rotation member) utilized by several implant holder embodiments disclosed herein.

FIG. 6 a top view of an exemplary implementation of an implant holder shaft 300 (or rotation member) utilized by several implant holder embodiments disclosed herein. Referring to FIG. 6, the sleeve 200 comprises a rod 310 featuring, at its proximal end, an in-hole stabilizer 314, a mating collar 312, and a rotation knob 316. At its distal end, the rod 210 further comprises a threaded post 318 for engaging the threaded hole 112 of the implant holder clamp 100.

Figure 7:
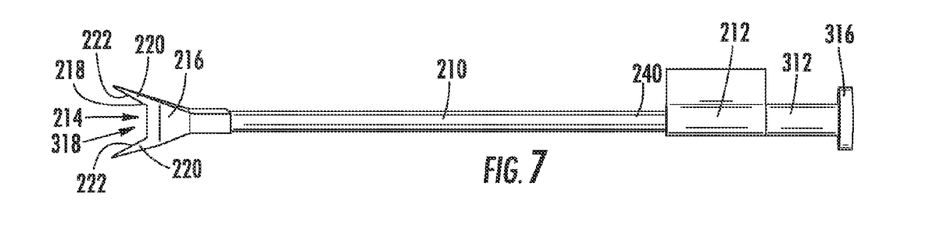
FIG. 7 is a top view of the shaft of FIG. 6 translationally and rotationally coupled with the sleeve of FIG. 5.

FIG. 7 is a top view of the shaft 300 of FIG. 6 translationally and rotationally coupled with the sleeve 200 of FIG. 5, such that the distal end of the shaft (featuring the threaded post 318) is inserted through the proximal opening of the hollow channel 214 and runs the length of the sleeve 200 to distal end, wherein the sleeve 200 circumferentially and encloses the distal and medial portions of the shaft 300.

Figure 8A:
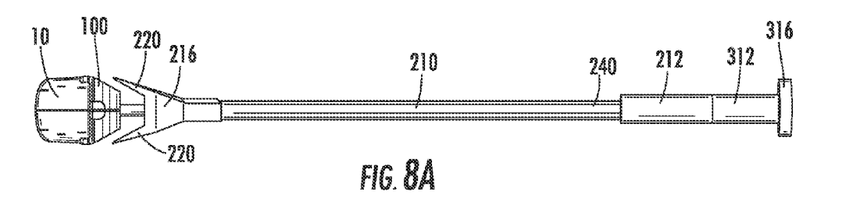
FIG. 8A is top view of the sleeve and shaft combination of FIG. 7 coupled to the clamp and implant combination of FIGS. 4B and 4C in an unlocked configuration.
Figure 8B:
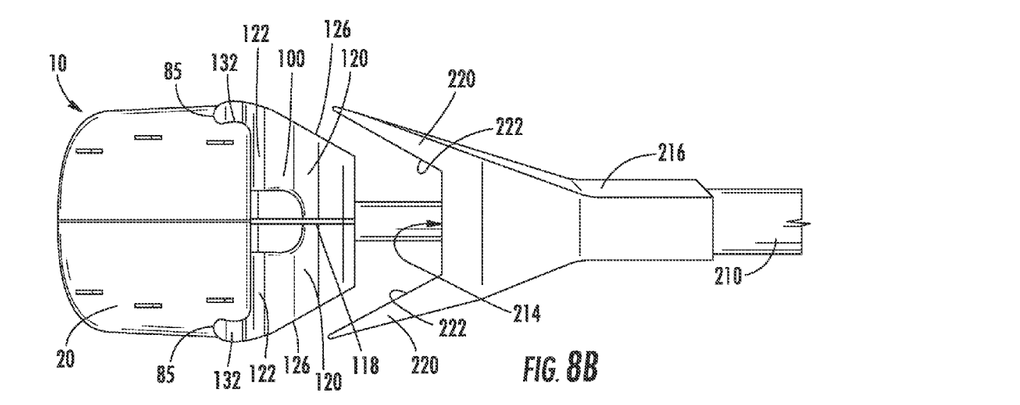
FIG. 8B is top view of the distal end of the sleeve and shaft combination coupled to the clamp and implant combination in the unlocked configuration illustrated in FIG. 8A.

FIG. 8A is top view of the sleeve 200 and shaft 300 combination of FIG. 7 (also referred to herein as the "locking mechanism") coupled to the clamp 100 and implant 10 combination of FIGS. 4B and 4C in an unlocked configuration. FIG. 8B is top view of the distal end of the sleeve and shaft combination coupled to the clamp and implant combination in the unlocked configuration illustrated in FIG. 8A. Referring to FIGS. 8A and 8B (collectively referred to herein as "FIG. 8"), the stem 110 (not shown) of the implant holder 100 movably resides in the distal opening of the hollow channel 214 proximate to the terminus surface 218 of the sleeve 200, and the threaded hole 112 of the implant holder 100 is partially coupled to the threaded post 318 of the shaft 300. As the shaft 300 continues to be rotated (via the rotation knob 316 in a tightening direction), the threaded post 318 will continue draw the stem 110 (not shown) into the hollow channel 214 and move the implant holder 100 and its pair of locking surfaces 126 closer and closer to the clamp coupler 216 and its locking surfaces 222. As such, rotating the shaft 300 within the sleeve 200 permits the surgeon (or a skilled assistant) to selectively determine to lock or unlock the clamp 100 which, in turn, determines whether the implant 10 is fixedly coupled (when locked) or loosely coupled (when unlocked) to the clamp 100.

Figure 9A:
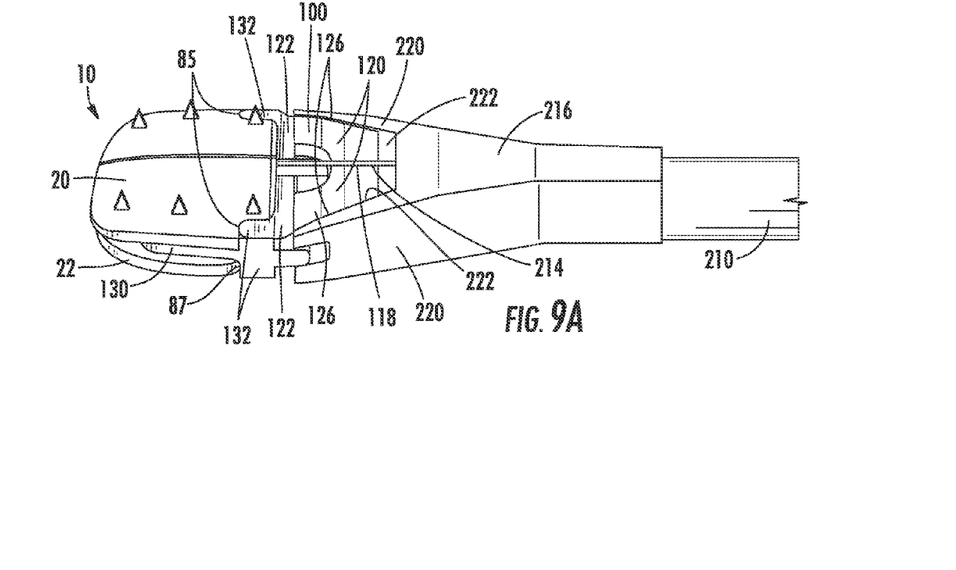
FIG. 9A is perspective view of the implant and the distal end of the implant holder (comprising the clamp, sleeve, and shaft) of FIGS. 8A and 8B in a locked configuration.
Figure 9B:
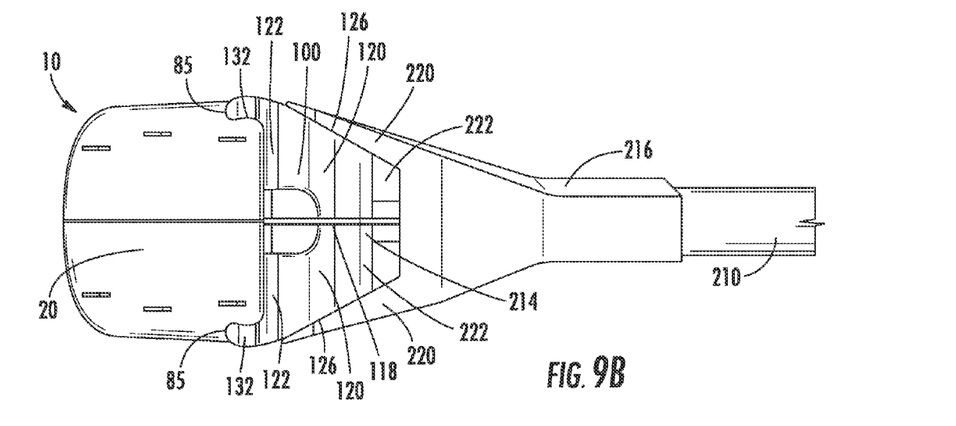
FIG. 9B is top view of the implant and the distal end of the implant holder (comprising the clamp, sleeve, and shaft) in the locked configuration illustrated in FIG. 9A.

FIG. 9A is perspective view of the implant 10 and the distal end of the implant holder (comprising the clamp 100, sleeve 200, and shaft 300) of FIGS. 8A and 8B in a locked configuration. FIG. 8B is top view of the implant 10 and the distal end of the implant holder (comprising the clamp 100, sleeve 200, and shaft 300) in the locked configuration illustrated in FIG. 9A. Referring to FIGS. 9A and 9B (collectively referred to herein as "FIG. 9"), the stem 110 (not shown) of the implant holder 100 has been maximally retracted into the distal opening of the hollow channel 214 proximate to the terminus surface 218 of the sleeve 200 by rotation of the threaded post 318 via the rotation knob 316. In this configuration, the implant holder's 100 pair of locking surfaces 126 are in direct contact with the clamp coupler's 216 locking surfaces 222 which, in turn, prevents the arms 102 and 104 (not shown) and their corresponding clamping elements 132 from flexibly opening and decoupling from the implant 10—that is, the implant 10 is "locked" or fixedly coupled to the clamp 100 of the implant holder (i.e., in a "locked position"). As such, the surgeon may emplace, move, and even withdraw the implant 10 and implant holder clamp 100 using surgeon force without leaving the implant 10 behind (as would be the case in an unlocked configuration) or risking the implant 10 from becoming inadvertently decoupled from the clamp 100.

To unlock the implant 10 from the clamp 100—such as when the surgeon has satisfactorily emplaced the implant 10 into the intervertebral space 14, for example—the surgeon merely rotates the shaft 200 in a loosening direction opposite the tightening direction (via the rotation knob 316) to separate the locking surfaces 126 of the implant holder clamp 100 from the locking surfaces 222 of the implant holder sleeve 200 and again return to a configuration akin to that shown in FIG. 8, in which instance the implant 10 is again only loosely coupled to the clamp 100 and can be removed by surgeon force from the clamp 100.

Figure 10A:
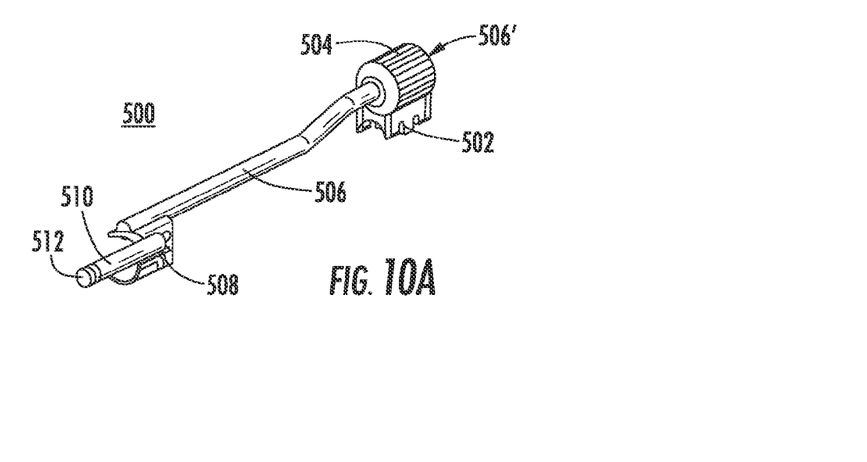
FIG. 10A is a perspective view of an exemplary implementation of an implant holder emplacement stop system utilized by certain implant holder embodiments disclosed herein.
Figure 10B:
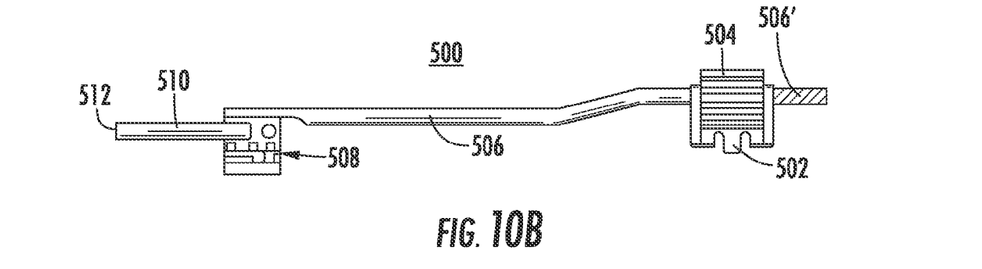
FIG. 10B is a side elevation view of the exemplary implementation of the stop system of FIG. 10A.
Figure 10C:
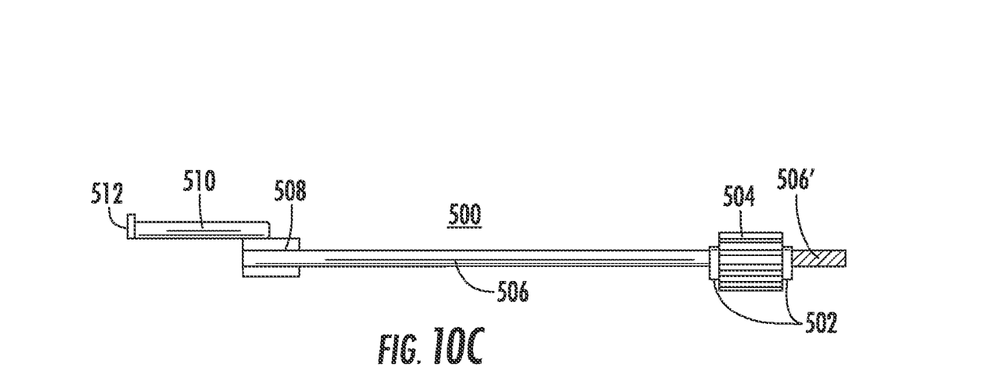
FIG. 10C is a top elevation view of the exemplary implementation of the stop system of FIGS. 10A and 10B.

FIG. 10A is a perspective view of an exemplary implementation of an implant holder emplacement stop system 500 utilized by certain implant holder embodiments disclosed herein. FIG. 10B is a side elevation view of the exemplary implementation of the stop system 500 of FIG. 10A. FIG. 10C is a top elevation view of the exemplary implementation of the stop system of FIGS. 10A and 10B. Referring to FIGS. 10A, 10B, and 10C (collectively referred to herein as "FIG. 10"), the stop system comprises a clip 502 for clipping to an attachment surface 240 of an implant holder sleeve 200 and rotatably mounting a threaded rotor 504 engaging the threaded proximal end 506' of a stop body 506. The distal end of the stop body 506 is coupled to a slidable sleeve 508 that, in turn, is coupled to a stop rod 510 ending in a stop surface 512 comprising the most distal end of the stop system 500. For certain embodiments, the stop system 512 may be used to reduce risk of penetration into spinal canal during the implantation procedure.

Figure 11A:
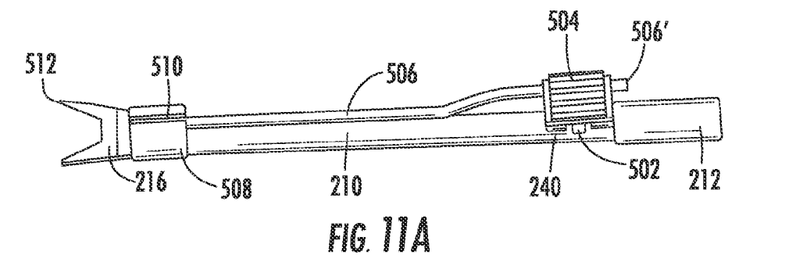
FIG. 11A is a perspective view of the exemplary implementation of an implant holder emplacement stop system of FIGS. 10A, 10B, and 10C connectively coupled to the top side of the implant holder sleeve of FIG. 5.
Figure 11B:
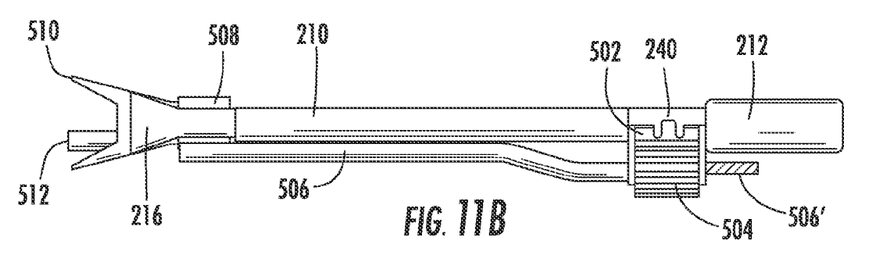
FIG. 11B is a perspective view of the exemplary implementation of an implant holder emplacement stop system of 11A in an alternative configuration connectively coupled to the bottom side of the implant holder sleeve.
Figure 11C:
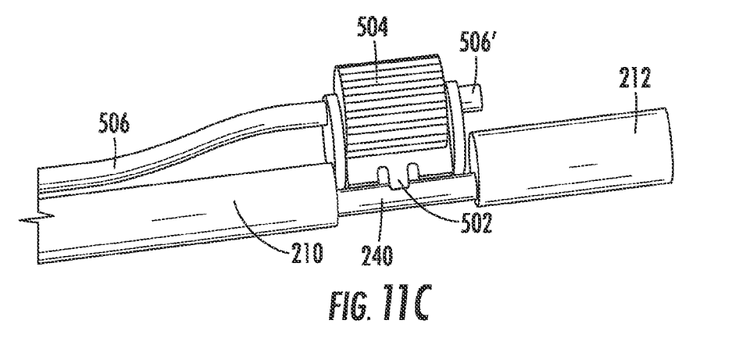
FIG. 11C is a perspective view of the proximal end of the stop system illustrated in FIG. 11A.

FIG. 11A is a perspective view of the exemplary implementation of an implant holder emplacement stop system of FIGS. 10A, 10B, and 10C connectively coupled to the top side of the implant holder sleeve 200 of FIG. 5. FIG. 11B is a perspective view of the exemplary implementation of an implant holder emplacement stop system of 11A in an alternative configuration connectively coupled to the bottom side of the implant holder sleeve. FIG. 11C is a perspective view of the proximal end of the stop system illustrated in FIG. 11A. Referring to FIGS. 11A, 11B, and 11C (collectively referred to herein as "FIG. 11"), by rotating the threaded rotor 504 the surgeon can longitudinally move the stop 512 to correspond to a desired depth such that when used, the stop will abut up against the anterior surface of a vertebrae (such as superior vertebral body 12a) and prevent the implant 10 from being emplaced any deeper into the intervertebral space 14.

Figure 12:
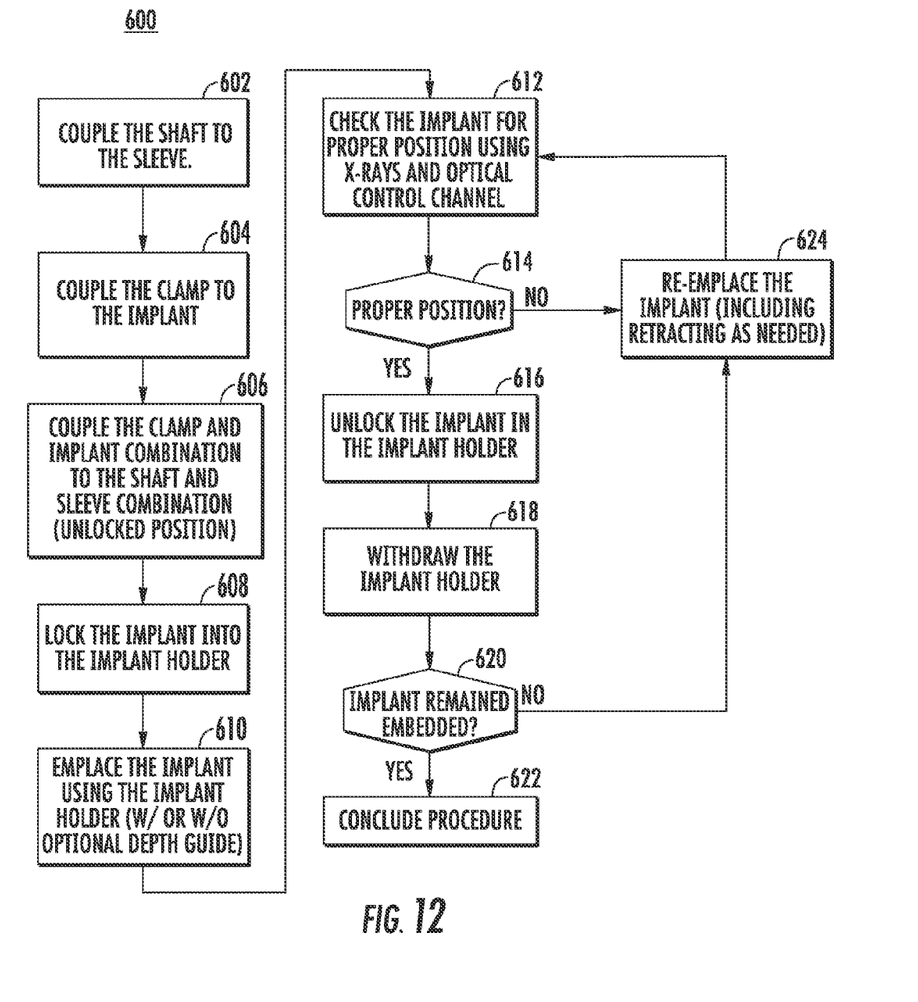
FIG. 12 is an operational flow diagram illustrating a method for emplacing an implant using certain embodiments of the implant holder disclosed herein.

FIG. 12 is an operational flow diagram illustrating a method for emplacing an implant 10 using certain embodiments of the implant holder disclosed herein. Referring to FIG. 12, at 602 the surgeon (or a qualified assistant) couples the shaft 300 to the sleeve 200 by inserting the shaft 300 into the sleeve 200 as previously discussed herein. At 604, the surgeon also couples (that is, loosely couples in an unlocked configuration) the clamp 100 to the implant 10. At 606 the surgeon them coupled the clamp 100 and implant 10 combination to the sleeve 200 and shaft 300 combination (or "locking mechanism") which initially is still in the unlocked configuration (or "unlocked position"). In an alternative approach, the surgeon could first couple the clamp, sleeve, and shaft in an unlocked configuration, and then couple this three-part assembly to the implant. In other words, there are several ways in which each of the clamp 100, sleeve 200, shaft 300, and implant 10 are coupled, and thus the order presented in FIG. 12 is only exemplary and is in no way limiting.

At 608 the surgeon then locks the implant 10 into the implant holder by engaging the locking surfaces 126 of the clamp 100 with the locking surfaces 222 of the sleeve 200 and, at 610, the surgeon then proceeds to emplace the implant 10 using the assembled implant holder (with or without the optional stop system 500). After emplacing the implant 10, the surgeon then uses X-rays (and the optical control channel 122 as an X-ray-visible reference point) to determine if the implant is emplaced in a suitable location. If not (as determined at 614), at 624 the surgeon reiteratively re-emplaces the implant 10 by continuing to manipulate the implant 10 via the implant holder and, returning to 612, checking implant 10 until it is properly emplaced.

Once properly emplaced, at 616 the implant 10 and implant holder are unlocked and, at step 618, the implant holder is withdrawn (or retracted) using surgeon force. At 620, if the embedding of the implant 10 is stable, the implant should remain embedded and, if so, the surgeon can then conclude the embedding portion of the procedure. However, if the implant 10 is not stable and continues to be loosely coupled to the implant holder when withdrawn, then the surgeon needs to re-emplace the implant (or a different implant) at step 624 and continue again from there.

As will readily appreciated by those of skill in the art, the various components described herein can be formed from a variety of biocompatible materials, such as cobalt chromium molybdenum (CoCrMo), titanium and titanium alloys, stainless steel or other metals, as well as ceramics or polymers such as polyetheretherketone (PEEK), polyetherketoneketone (PEKK), bioresorbable materials, and bonegraft (for example allograft and xenograft). A coating may be added or applied to the various components described herein to improve physical or chemical properties, or to help ensure bony in or on growth of medication. Examples of coatings include plasma-sprayed titanium coating or Hydroxypatite. Moreover, skilled artisans will also appreciate that the various components herein described can be constructed with any dimensions desirable for implantation of any intervertebral space along the spine and, in addition to use as a disc replacement device, are also readily configurable for use with a range of bone-anchored orthopedic prostheses, such as a spinal fusion implant, an interbody spacer, an intervertebral cage, a corpectomy device, hip and knee replacement implants, long bone replacement plates, intramedulary nails and rods, bone fixation plates (such as for fixation of craniomaxillofacial fractures), veterinary implants, and tips for guide wires, and the like.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. An implant holder for an implant device, the implant holder comprising:
   a clamp for coupling to and decoupling from the implant device, the clamp including:

a central body having an interface for coupling with the implant device; and a stem extending from a proximal end of the central body, a proximal end of the stem including a stem mating feature;

the central body including a first arm and a second arm extending from the stem, the first arm and the second arm each including a central spacer portion having a thickness less than the thickness of each of the respective first and second arms, the central spacer portion sized and configured to abut at least one of an upper endplate and a lower endplate of the implant device, such that a longitudinal line of the upper endplate and the lower endplate of the implant device is maintained in a parallel configuration with respect to a longitudinal line of the clamp, the first arm and the second arm each including an exterior locking surface extending at an acute angle with respect to a longitudinal axis of the implant holder and a projection extending from and contained on the locking surface in a direction parallel to the longitudinal axis of the implant holder; and a locking mechanism including:

a hollow sleeve having an opening at a distal end of the hollow sleeve, the opening sized and configured to translationally and rotationally receive at least a portion of the stem;

a clamp coupler attached to the distal end of the hollow sleeve, the clamp coupler including a pair of locking tines each defining a corresponding locking surface each sized and configured to mate with a corresponding one of the exterior locking surfaces of the central body, wherein said locking surfaces of the locking tines extend at an acute angle with respect to a longitudinal axis of the implant holder, the locking surfaces of the locking tines including recesses extending through the locking tines in a direction perpendicular to the longitudinal axis of the implant holder, the recesses sized and configured to mate with the corresponding projections extending from the exterior locking surfaces of the clamp; and a shaft translationally and rotationally received within the hollow sleeve along a central axis of the implant holder, a distal end of the shaft including a shaft mating feature sized and configured to mate with the stem mating feature;

wherein the locking mechanism, in a first position, causes the central body to mate with the clamp coupler locking the clamp to the implant device such that the clamp cannot be decoupled from the implant device; and wherein the locking mechanism, in a second position, causes the central body to be located apart from the clamp coupler unlocking the clamp from the implant device such that the clamp remains coupled to the implant device in the absence of a sufficient decoupling force but the clamp is decoupled from the implant device with the application of the sufficient decoupling force.

2. The implant holder of claim 1 wherein the stem mating feature comprises a threaded hole, and wherein the shaft mating feature comprises a threaded post for engaging the threaded hole.

3. The implant holder of claim 1 wherein the decoupling force is a surgeon force.

4. The implant holder of claim 1 wherein the implant holder is comprised of a radio-opaque material, and wherein the implant holder comprises an X-ray-visible reference point visible in an X-ray corresponding to the position of the implant device.

5. The implant holder of claim 4 wherein the X-ray-visible reference point comprises a channel located on a surface of the central body of the clamp.

6. The implant holder of claim 4 wherein the radio-opaque material is metal.

7. The implant holder of claim 1 further comprising a stop system including a stop rod for abutting an interior surface of the patient during insertion of the implant device.

8. The implant holder of claim 7 wherein the stop system is attachable to the locking mechanism.

9. The implant holder of claim 1 wherein the first arm and the second arm define a U-shaped interface for coupling with the implant, wherein the first and second arms are coupled to the stem proximate a flexion hole.

10. The implant holder of claim 9 wherein the first and second arms are separated from each other by a lateral gap extending from the flexion hole to the distal end of the central body of the clamp.

11. The implant holder of claim 1 wherein the clamp coupler includes a terminus surface, wherein the locking tines and the terminus surface are sized and configured to correspond to a proximal surface of the central body of the clamp.

12. An implant holder apparatus comprising:

a clamp for engaging an implant device such that the clamp remains coupled to the implant device until a sufficient decoupling force is applied to decoupled the implant device from the clamp, the clamp including:

a central body having an interface for coupling with the implant device; and a stem extending from a proximate end of the central body, a proximate end of the stem including a stem mating feature;

the central body including a first arm and a second arm extending from the stem, the first arm and the second arm each including a central spacer portion having a thickness less than the thickness of each of the respective first and second arms, the central spacer portion sized and configured to abut at least one of an upper endplate and a lower endplate of the implant device, such that the upper endplate and the lower endplate are maintained in a parallel configuration when coupled to the clamp, the first arm and the second arm including a first pair of locking surfaces extending at an acute angle with respect to a longitudinal axis of the implant holder and a projection extending from and contained on each of the pair of locking surfaces in a direction parallel to the longitudinal axis of the implant holder;

a sleeve for locking and unlocking the clamp such that the implant device cannot be decoupled from the clamp when locked but can be decoupled from the clamp when unlocked and when a sufficient decoupling force is applied, the sleeve including:

a hollow body portion extending between a proximal end and a distal end, an opening at the distal end sized and configured to translationally and rotationally receive at least a portion of the stem; and a clamp coupler attached to the distal end sized and configured to mate with a proximal surface of the central body of the clamp, the clamp coupler including a pair of locking tines each defining a corresponding second pair of locking surfaces sized and configured to mate with a corresponding one of the projections extending from the first pair of locking surfaces; a shaft for selectively determining to lock or unlock the clamp, the shaft including
   an elongated body portion sized and configured to be translationally and rotationally received within the hollow body portion of the sleeve along a central axis of the implant holder;
   a shaft mating feature located at a distal end of the elongated body portion sized and configured to mate with the stem mating feature;
wherein the sleeve and the shaft are fixed with respect to each other in a longitudinal direction along the central axis of the implant holder;
wherein rotation of the shaft causes the shaft mating feature to engage the stem mating feature such that the stem is drawn into the hollow body portion of the sleeve and the clamp coupler is mated with the central body of the clamp, thereby locking the implant device at the clamp interface.

13. The apparatus of claim 12 wherein the clamp interface engages external engagement features of the implant device.

14. The apparatus of claim 12 wherein the clamp comprises at least two central projecting clamping elements.

15. The apparatus of claim 14 wherein the at least two central-projecting clamping elements further comprise:
   at least two central-projecting clamping elements for engaging an upper endplate of the implant device; and
   at least two central-projecting clamping elements for engaging a lower end plate of the implant device.

16. The apparatus of claim 12 wherein the clamp further comprises a U-shaped central spacer to provide temporary stability for the implant device for emplacement.

17. The apparatus of claim 12 wherein the clamp is coupled to the implant device before being operatively coupled to the sleeve or to the shaft.

18. The apparatus of claim 12 wherein the shaft comprises a rotation knob for the application of a rotation force to the shaft.

19. The apparatus of claim 18 wherein rotating the shaft in a tightening direction both increasingly engages the stem mating feature and transitions the implant holder from unlocked to locked.

20. The apparatus of claim 12 wherein the sleeve and the clamp are oriented such that the sleeve and clamp are drawn together into a locked position by rotation of the shaft in a tightening direction.

21. The apparatus of claim 12, wherein locking the clamp occurs when the first pair of locking surfaces and the second pair of locking surfaces are moved into contact, and
   wherein unlocking the clamp occurs when the first pair of locking surfaces and the second pair of locking surfaces are separated after being in contact.

22. The apparatus of claim 21,
   wherein the first pair of locking surfaces and the second pair of locking surfaces are moved into contact by the rotation of the shaft in a tightening direction, and
   wherein the first pair of locking surfaces and the second pair of locking surfaces are separated after being in contact by the rotation of the shaft in a loosening direction.

* * * * *